US00PP25951P3

(12) United States Plant Patent
Zaiger et al.

(10) Patent No.: US PP25,951 P3
(45) Date of Patent: Sep. 29, 2015

(54) PEACH TREE NAMED 'SUMMER FROST'

(50) Latin Name: *Prunus persica*
Varietal Denomination: Summer Frost

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 100 days.

(21) Appl. No.: 13/999,133

(22) Filed: Jan. 22, 2014

(65) Prior Publication Data

US 2015/0208563 P1 Jul. 23, 2015

(51) Int. Cl.
*A01H 5/00* (2006.01)

(52) U.S. Cl.
USPC ..... Plt./195

(58) Field of Classification Search
USPC ..... Plt./195
See application file for complete search history.

*Primary Examiner* — Annette Para

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit with attractive red skin color.
4. Fruit with firm, white flesh.
5. Fruit with good flavor and eating quality.
6. Fruit with good storage and handling quality.

1 Drawing Sheet

Botanical designation: *Prunus persica.*
Variety denomination: 'SUMMER FROST'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Glacier' Peach (U.S. Plant Pat. No. 11,868) and our proprietary non-patented peach seedling selections with the field identification numbers '348LN91', '184LT327', '211LK86', '226LK505' and '245LK134'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between our proprietary non-patented peach seedling selections with the field identification numbers '348LN91' and '184LT327'. The seed parent '348LN91' peach (non-patented) originated from open pollinated seed collected from our proprietary non-patented peach seedling with the field identification number '245LK134'. The pollen parent '184LT327' peach (non-patented) originated as a first generation cross between our proprietary non-patented peach seedlings with the identification numbers '211LK86' and '226LK505'. A large number of seeds from this first generation cross were grown and maintained on their own root system and under close and careful observation one such seedling which is the present variety, exhibited desirable tree ad fruit characteristics and was selected in 2007 for additional asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a regular and productive bearer of large size, firm, white flesh, clingstone fruit.

The fruit is further characterized by having good flavor and eating quality, having an attractive red skin color and being relatively uniform in size throughout the tree. In comparison to its seed parent '348LN91' peach (non-patented), the fruit of the new variety is larger in size and is approximately 8 weeks earlier in maturity. In comparison to its pollen parent '184LT327' peach (non-patented) the fruit of the new variety is white flesh compared to yellow and is approximately 2 weeks later in maturity. In comparison to the commercial variety 'Glacier' Peach (U.S. Plant Pat. No. 11,686) the fruit of the new variety is larger in size and is approximately 9 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 6 year old specimens grown near Modesto, Calif., with color in accordance with Munsell Book of Color published in 1958.

Tree:

*Size.*—Medium, usually pruned to 3 to 3.5 meters in height and width for economical harvesting of fruit. Size varies with different cultural practices.

*Vigor.*—Vigorous, growth of 1.5 to 2.5 meters the first growing season. Varies slightly with type and fertility of soil, climatic conditions and cultural practices.

*Form.*—Upright, usually pruned to vase shape.

*Branching habit.*—Upright, crotch angle approximately 35°, increases with heavy crop load.

*Productivity.*—Productive, normal fruit thinning and spacing necessary for marketable size fruit. Number of fruit set varies with climatic conditions during blooming period.

*Bearer.*—Regular, adequate fruit set 4 consecutive years. No alternate bearing observed.

*Fertility.*—Self fertile.

*Density.*—Medium dense, usually pruned to vase shape to increase air movement and sunlight to enhance fruit color and health of fruit wood.

*Hardiness.*—Hardy in all stone fruit growing areas of California. Tree grown in USDA Hardiness Zone 9. Winter chilling requirement approximately 750 hours at or below 45° F.

Trunk:

*Size.*—Large. Average circumference 46.0 cm at 20.3 cm above ground on a 6 year old tree.

*Stocky.*—Medium stocky.

*Texture.*—Medium shaggy, roughness increases with age.

*Color.*—Varies from 10YR 3/2 to 2.5Y 5/2.

Branches:

*Size.*—Medium. Average circumference 12.2 cm at 1.2 meters above ground on a 6 year old tree. Crotch angle approximately 35°, increases with heavy crop load.

*Surface texture.*—New growth relatively smooth. Mature growth medium rough, roughness increases with age.

*Lenticels.*—Average number 22 in a 25.8 sq cm section. Average length 4.0 mm. Average width 1.7 mm. Color varies from 7.5YR 6/10 to 10YR 6/8.

*Color.*—New growth varies from 5GY 5/6 to 7GY 6/6. Old growth varies from 5YR 3/2 to 10YR 3/4, varies with age of growth.

Leaves:

*Size.*—Large. Average length 132.8 mm. Average width 43.9 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins. Lower surface relatively smooth, except for small ridges created by midrib and pinnate venations. Both upper and lower surfaces glabrous.

*Petiole.*—Average length 10.4 mm. Average width 1.6 mm. Longitudinally grooved. Surface glabrous. Color varies from 5GY 6/6 to 5GY 5/6.

*Glands.*—Type — reniform. Size — medium. Average length 1.0 mm. Average diameter 0.8 mm. Number varies from 2 to 4, average number 3. Located primarily on the base of leaf blade and upper portion of petiole. Color varies from 5GY 5/6 to 5GY 4/6.

*Stipules.*—Average number 2. Average length 4.2 mm. Edges — pectinate. Color varies from 5GY 6/6 to 5GY 5/6.

*Color.*—Upper surface varies from 7.5GY 3/4 to 7.5GY 2/4. Lower surface varies from 5GY 4/4 to 7.5GY 4/4. Midvein color varies from 2.5GY 9/4 to 5GY 8/6.

Flower buds:

*Size.*—Large. Average length 22.5 mm. Average diameter 11.5 mm.

*Hardiness.*—Hardy with respect to California winters.

*Form.*—Elongated.

*Pedicel.*—Average length 4.5 mm. Average width 1.2 mm. Color varies from 2.5GY 7/6 to 2.5GY 6/6.

*Color.*—Varies from 5RP 7/8 to 5RP 7/10.

Flowers:

*Blooming period.*—Date of First Bloom Feb. 23, 2013. Date of Petal Fall Mar. 5, 2013, varies slightly with climatic conditions.

*Size.*—Large. Average height 22.6 mm. Average diameter 52.3 mm.

*Petals.*—Normally 5, alternately arranged to sepals. Size — large. Average length 26.2 mm. Average width 23.3 mm. Form — globose, narrowing at point of attachment. Margin — sinuate. Arrangement — free. Color varies from 5RP 8/4 to 5RP 7/6. Both upper and lower surfaces glabrous.

*Sepals.*—Normally 5, alternately arranged to petals. Size — large. Average length 6.7 mm. Average width 5.7 mm. Shape — ovate. Margin — entire. Color — upper surface varies from 5GY 5/8 to 5R 3/6. Lower surface varies from 5R 2/4 to 7.5R 2/4. Upper surface glabrous, lower surface pubescent.

*Stamens.*—Average number per flower 40, varies from 39 to 41. Average filament length 15.0 mm. Filament color varies from N 9.5/(white) to 5RP 5/10. Anther color varies from 5Y 8/8 to 7.5R 4/10.

*Pollen.*—Self fertile. Color varies from 5Y 8/10 to 5Y 7/10.

*Pistil.*—Normally 1. Surface — pubescent. Average length 18.1 mm. Position of stigma an average 1.1 mm below anthers. Color varies from 7.5Y 8.5/4 to 7.5Y 8.5/6.

*Fragrance.*—Heavy.

*Color.*—Varies from 5RP 8/4 to 5RP 7/6.

*Number flowers per flower bud.*—One.

*Pedicel.*—Average length 4.4 mm. Average width 1.5 mm. Color varies from 2.5GY 6/6 to 5GY 6/6.

Fruit:

*Maturity when described.*—Firm ripe.

*Date of first picking.*—Jul. 21, 2013.

*Date of last picking.*—Jul. 31, 2013, varies slightly with climatic conditions.

*Size.*—Large. Average diameter axially 72.1 mm. Average transversely in suture plane 80.0 mm. Average weight 267.0 grams, varies slightly with fertility of the soil, amount of thinning and climatic conditions.

*Form.*—Globose.

*Suture.*—Nearly smooth, some fruit with slight suture.

*Ventral surface.*—Nearly smooth.

*Apex.*—Retuse.

*Base.*—Retuse.

*Stem cavity.*—Rounded to slightly elongated in suture plane. Average depth 9.4 mm. Average diameter 9.4 mm.

Stem:

*Size.*—Small to medium. Average length 9.0 mm. Average diameter 3.2 mm.

*Color.*—Varies from 5GY 5/8 to 7.5GY 5/8.

Flesh:

*Ripens.*—Evenly.

*Texture.*—Firm, meaty.

*Fibers.*—Few, small, tender.

*Firmness.*—Firm, comparable to other commercial peach varieties.

*Aroma.*—Moderate.

*Amydgalin.*—Undetected.

*Eating quality.*—Good.

*Flavor.*—Good.

*Juice.*—Moderate amount, enhances flavor.

*Brix.*—Average Brix 11.1°, varies slightly with amount of fruit per tree and climatic conditions.

*Color.*—Varies from 7.5Y 9/2 to N 9.5/(white).

*Pit cavity.*—Average length 34.2 mm. Average width 25.3 mm. Average depth 10.2 mm. Color varies from 5R 3/10 to 7.5R 3/10.

Skin:

*Thickness.*—Medium.

*Surface.*—Slightly waffled.

*Pubescence.*—Moderate amount, short in length.

*Tendency to crack.*—None.

*Color.*—Ground color varies from 5Y 8.5/4 to 5Y 8.5/6. Overspread with 7.5R 3/4 to 10R 4/8.

*Tenacity.*—Tenacious to flesh.

*Astringency.*—None.

Stone:

*Type.*—Clingstone.

*Size.*—Large. Average length 33.2 mm. Average width 24.3 mm. Average thickness 18.4 mm.

*Form.*—Ovoid.

*Base.*—Flat.

*Apex.*—Pointed. Average length 1.4 mm.

*Surface.*—Pitted throughout, pits vary from rounded to slightly elongated.

*Sides.*—Unequal, with one side extending further from suture plane.

*Ridges.*—Small ridges extending from base toward, apex.

*Tendency to split.*—None.

*Color.*—Varies from 5YR 3/4 to 7.5YR 3/4 when dry.

Kernel:

*Size.*—Large. Average length 18.7 mm. Average width 12.2 mm. Average depth 5.7 mm.

*Form.*—Ovoid.

*Viability.*—Viable, complete embryo development.

*Skin color.*—Varies from 5Y 9/4 to 7.5Y 9/4.

Use:

*Dessert.*—Market — local and long distance.

Keeping quality: Good, held firm in cold storage at 38° to 42° F. for 3 weeks without internal breakdown or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

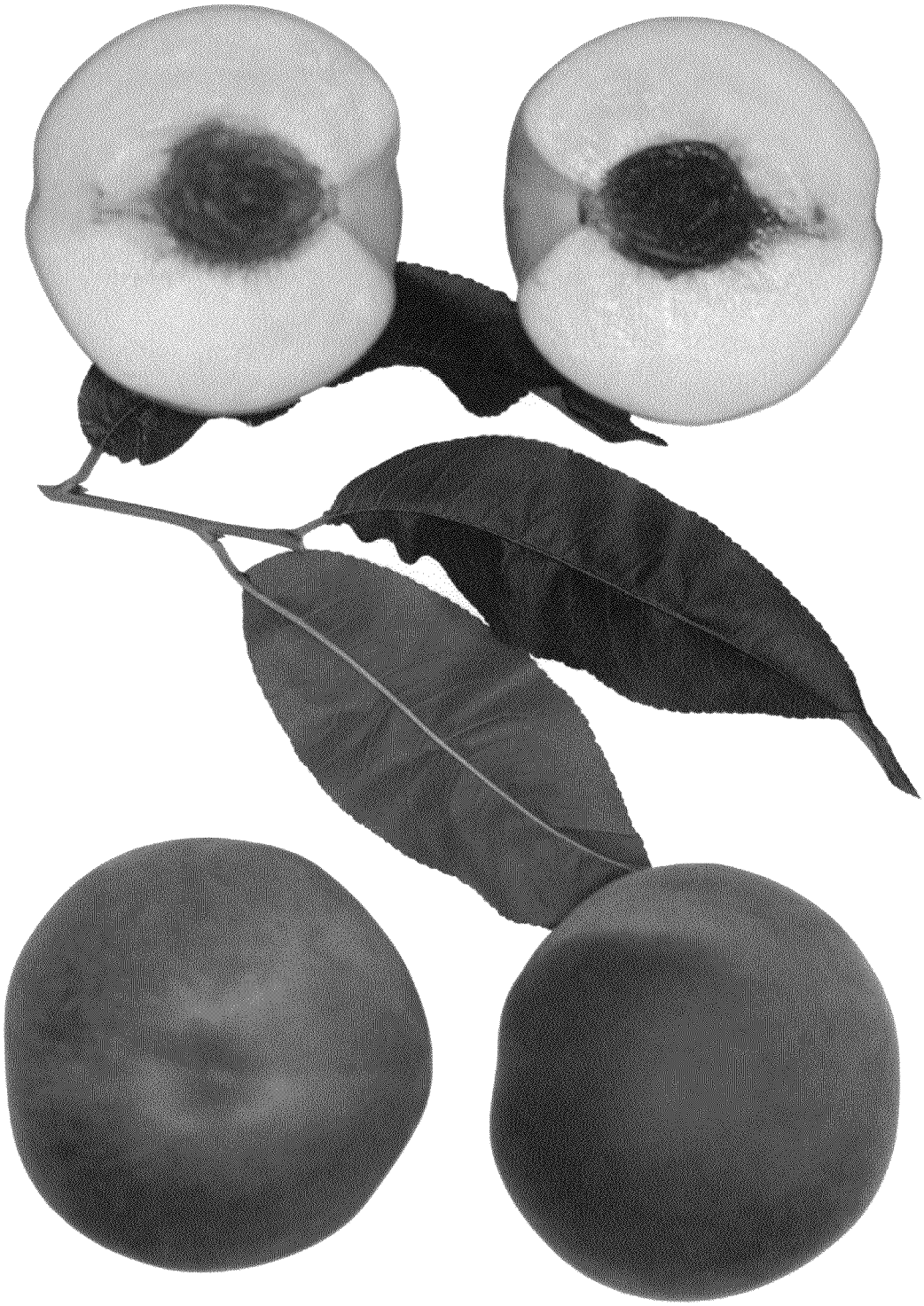

* * * * *